United States Patent
Ho et al.

(10) Patent No.: US 11,338,102 B2
(45) Date of Patent: May 24, 2022

(54) DETERMINING FACIAL METRICS OF A PATIENT AND IDENTIFYING A CUSTOM MASK FOR THE PATIENT THEREFROM

(71) Applicant: KONINKLIJKE PHILIPS N.V., Eindhoven (NL)

(72) Inventors: Peter Chi Fai Ho, Pittsburgh, PA (US); Richard Thomas Haibach, Verona, PA (US); Daniel Steed, North Huntingdon, PA (US); Robert William Baiko, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 831 days.

(21) Appl. No.: 16/220,043

(22) Filed: Dec. 14, 2018

(65) Prior Publication Data
US 2019/0184122 A1     Jun. 20, 2019

Related U.S. Application Data

(60) Provisional application No. 62/607,484, filed on Dec. 19, 2017.

(51) Int. Cl.
*A61M 16/06*     (2006.01)
*A61B 5/107*     (2006.01)
(Continued)

(52) U.S. Cl.
CPC ....... *A61M 16/0616* (2014.02); *A61B 5/0064* (2013.01); *A61B 5/1077* (2013.01);
(Continued)

(58) Field of Classification Search
CPC ........... G06T 7/593; G06T 2207/30201; G06T 7/0012; G06V 40/168; G06V 40/173;
(Continued)

(56) References Cited

U.S. PATENT DOCUMENTS

| 2006/0023228 A1 | 2/2006 | Geng |
| 2014/0064579 A1 | 3/2014 | Lee |

(Continued)

FOREIGN PATENT DOCUMENTS

| CN | 103780843 A | 5/2014 |
| CN | 106056027 A | 10/2016 |
| WO | WO2017205903 A1 | 12/2017 |

OTHER PUBLICATIONS

FotoFinder Adonia, https://www.youtube.com/watch?v=c7rNenEnY64&t=43s (Year: 2015).*

(Continued)

*Primary Examiner* — Mark Roz
(74) *Attorney, Agent, or Firm* — Michael W. Haas

(57) ABSTRACT

A method of determining facial metrics of a patient includes: capturing a first image of the patient with an image capturing device positioned in a first known position with the assistance of a positioning device, capturing a second image of the patient with the image capturing device positioned in a second known position different that the first known position with the assistance of the positioning device, and determining facial metrics of the patient by analyzing the first image and the second image.

13 Claims, 6 Drawing Sheets

(51) Int. Cl.
*A61B 5/00* (2006.01)
*G06T 7/593* (2017.01)
*H04N 13/239* (2018.01)
*G06T 7/00* (2017.01)
*H04N 5/247* (2006.01)
*G01B 9/00* (2006.01)
*G01B 11/02* (2006.01)
*G06V 20/64* (2022.01)
*G06V 40/16* (2022.01)
*G16H 10/60* (2018.01)

(52) U.S. Cl.
CPC .......... *A61B 5/1079* (2013.01); *A61B 5/4818* (2013.01); *A61M 16/06* (2013.01); *A61M 16/0633* (2014.02); *A61M 16/0666* (2013.01); *G01B 9/00* (2013.01); *G01B 11/026* (2013.01); *G06T 7/0012* (2013.01); *G06T 7/593* (2017.01); *G06V 20/647* (2022.01); *G06V 40/168* (2022.01); *G06V 40/173* (2022.01); *H04N 5/247* (2013.01); *H04N 13/239* (2018.05); *A61B 5/6803* (2013.01); *A61B 2562/164* (2013.01); *A61M 16/0683* (2013.01); *A61M 2016/0661* (2013.01); *G01B 2210/52* (2013.01); *G06T 2207/30201* (2013.01); *G06V 40/165* (2022.01); *G06V 40/169* (2022.01); *G06V 40/171* (2022.01); *G16H 10/60* (2018.01)

(58) Field of Classification Search
CPC .. G06V 20/647; G06V 40/169; G06V 40/171; G06V 40/165; G01B 9/00; G01B 11/026; G01B 2210/52; A61M 2016/0661; A61M 16/0616; A61M 16/0633; A61M 16/0666; A61M 16/0683; A61B 5/0064; A61B 5/1077; A61B 5/1079; A61B 5/4818; A61B 5/6803; A61B 2562/164; H04N 13/239; H04N 5/247; G16H 10/60
USPC ........................................................ 382/203
See application file for complete search history.

(56) References Cited

U.S. PATENT DOCUMENTS

2015/0262422 A1   9/2015   Znamenskiy
2017/0173289 A1*  6/2017   Lucey .................... G16H 30/40

OTHER PUBLICATIONS

BGNing https://www.bgningoem.com/BGNing-Multi-function-Mobile-Phone-Stand-1-4-Tripod-Mount-3-Position-Bracket-for-Clip-Video-Live-Selfie-Stick-Smartphone-Camera-Monopod-p496199.html (Year: 2019).*
Broida, R. et al., "Use the Google Cardboard VR Headset with an iPhone", Article from CNET Google cardboard VR headset, Aug. 15, 2014 https://www.cnet.com/how-to/use-your-google-cardboard-vr-headset-w . . . .
"Virtual Reality Headsets", Hypergrid Business, Jun. 18, 2016 http://www.hypergridbusiness.com/faq/best-virtual-reality-headsets/.

* cited by examiner

DETERMINING FACIAL METRICS OF A PATIENT AND IDENTIFYING A CUSTOM MASK FOR THE PATIENT THEREFROM

CROSS-REFERENCE TO RELATED APPLICATIONS

This patent application claims the priority benefit under 35 U.S.C. § 119(e) of U.S. Provisional Application No. 62/607,484, filed on Dec. 19, 2017, the contents of which are herein incorporated by reference.

BACKGROUND OF THE INVENTION

1. Field of the Invention

The present invention pertains to methods for determining facial metrics of a patient and further identifying a custom mask for the patient therefrom. The present invention also pertains to positioning devices for use in such methods.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

In order to optimize treatments as well as patient compliance with such treatments it is important to provide the patient with a well fit mask. As no two patient's faces are exactly the same, the best way to ensure an optimum fit is to provide the patient a custom/semi-custom mask that is sized/designed according to their specific facial geometry. Such custom/semi-custom CPAP masks require a scan of the patient's face. The scan is a critical element to generating the custom geometry. In order to gather the geometry of the patient's face, a camera or scanner is required. Current scanner technologies require an expensive setup comprised of a fixture with more than one camera. Hand held 3-D scanners today are currently extremely expensive reaching 20K USD. As a result of the cost of such devices, access to such devices is generally limited.

SUMMARY OF THE INVENTION

As one aspect of the invention, a method of determining facial metrics of a patient is provided. The method comprises: capturing a first image of the patient with an image capturing device positioned in a first known position with the assistance of a positioning device; capturing a second image of the patient with the image capturing device positioned in a second known position different that the first known position with the assistance of the positioning device; and determining facial metrics of the patient by analyzing the first image and the second image.

The first image and the second image may comprise 2D images.

The image capturing device may comprise a camera of an electronic device. The electronic device may comprise one of a smartphone device or an electronic tablet. The smartphone or tablet may comprise a front-facing camera and a rear-facing camera and wherein the first image and the second image are each captured using the front facing camera. The smartphone or tablet may comprise a front-facing camera and a rear-facing camera and wherein the first image and the second image are each captured using the rear-facing camera.

The positioning device may comprise: an infrared projector; and an infrared sensor. The positioning device may be structured to provide an audible or visual feedback to the patient.

The positioning device may include secondary indicia indicating a position for engaging the patient with the positioning device and a position for placing the image capturing device in regard to the positioning device. The positioning device may be formed from a planar form having primary indicia for assisting in forming the positioning device from the planar form. The primary indicia may include an indication of where a cut or a fold is to be made to the planar form in order to form the positioning device.

The positioning device may comprise: a first elongate arm member having a first end and an opposite second end; an area for the patient to place their chin disposed at or about the first end; a handle coupled at or about the first end of the first elongate arm member, the handle structured to be grasped by the patient to hold the positioning device under the chin of the patient; a second elongate arm member having a first end coupled at or about the second end of the first elongate arm member and an opposite second end; a third elongate arm member having a first end coupled at or about second end of the first elongate arm member and an opposite second end; and a number of regions delineated on one or both of the second and third elongate arm members for receiving the image capturing device. One of the second or third elongate arm members includes a remotely operable image capturing device, and wherein capturing one of the first image or the second image is captured by the remotely operable image capturing device.

The positioning device may comprise: an elongated tray member having a generally J-shaped cross-section; and a plurality of securement means coupled to the tray member, each of the securement means structured to secure the tray member to a vertical surface, wherein the tray member is structured to support an image capturing device in a plurality of predetermined positions.

As another aspect of the present invention, a method for identifying a mask for a patient is provided. The method comprises: capturing a first image of the patient with an image capturing device positioned in a first known position with the assistance of a positioning device; capturing a second image of the patient with the image capturing device positioned in a second known position different that the first known position with the assistance of the positioning device; determining facial metrics of the patient by analyzing the first image and the second image; determining a mask for the patient using the determined facial metrics of the patient; and identifying the mask to the patient.

Identifying the mask to the patient may comprise providing the patient with a specification of the mask. Identifying the mask to the patient may comprise providing the patient with the mask.

DETAILED DESCRIPTION OF EXEMPLARY EMBODIMENTS

Figures 1A, 1B:
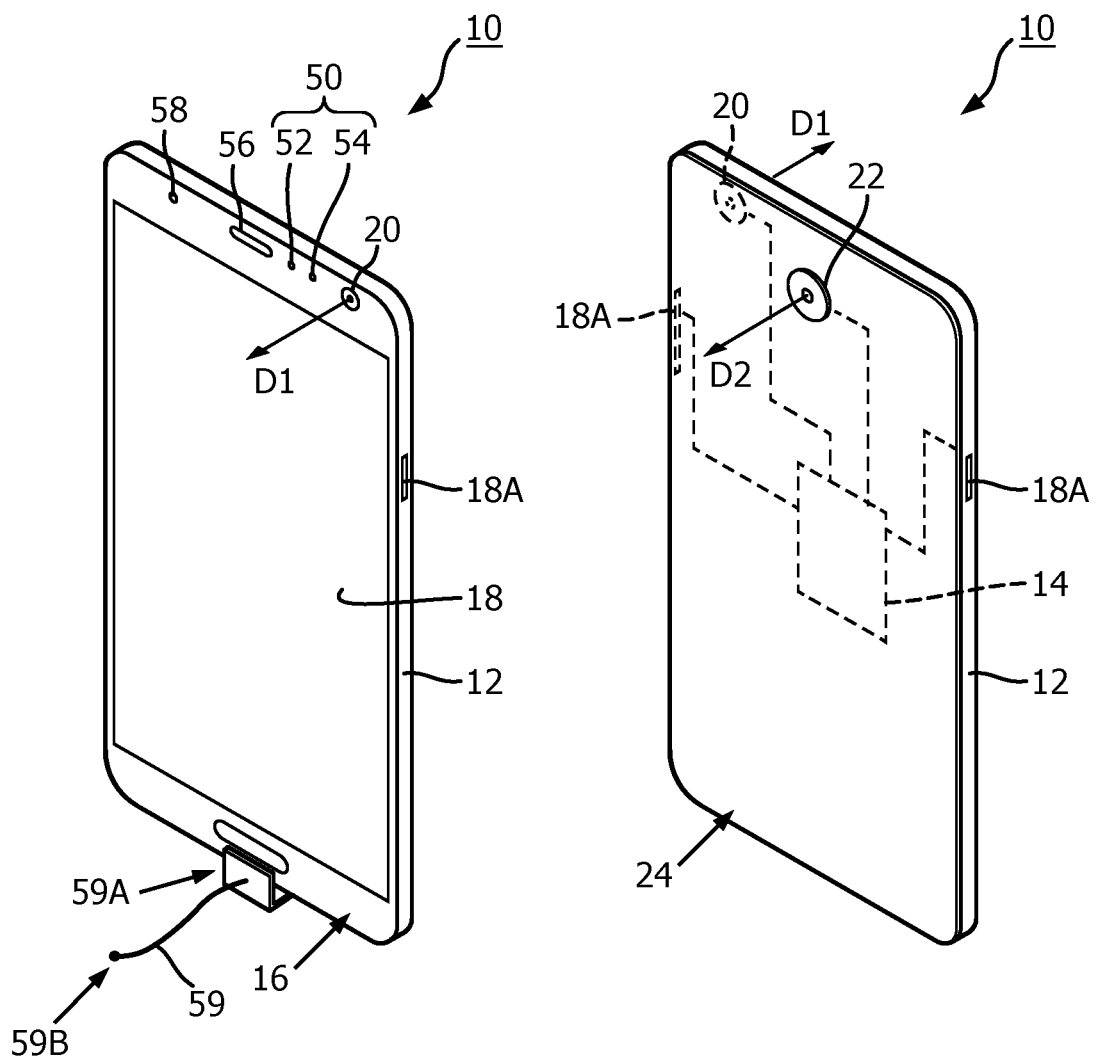
FIGS. 1A and 1B, respectively, are isometric front and rear views of an electronic device in the form of a smartphone in accordance with one example embodiment of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the term "image" shall refer to a representation of the form of a person or thing. Such representation may be a reproduction of the form or may be in the form of electronic information describing the form.

As used herein, the term "2-D image" shall refer to a two-dimensional representation of the form of a person or thing, whether in electronic form (e.g., such as stored in digital memory) or in visible form (e.g., displayed via an electronic display). A 2-D image may be captured of a physical object by using a digital camera or 2-D scanning device.

As used herein, the term "image registration", also referred to as "registering" is the process of aligning two or more images of the same scene. This process involves designating one image as the reference image, also called the fixed image, and applying geometric transformations or local displacements to the other images so that they align with the reference. By applying image registration to a series of at least two 2-D images of known focal distances, a 3-D model can be generated.

Embodiments of the present invention provide readily accessible, low-cost solutions for obtaining facial metrics of a patient, which may be used to identify a custom or semi-custom mask for the patient. Such embodiments utilize cameras on readily available electronic devices, e.g., without limitation, smartphones and electronic tablets, which typically have a front facing camera (i.e., a camera facing the user) and in many cases additionally have a rear-facing camera (i.e., a camera facing away from the user). Such cameras are used capture multiple 2-D images of the patient at predetermined distances which are then stitched together to form a 3-D model of the patient. Such 3-D model can then be employed in determining, and further identifying, a custom mask for use by the patient for receiving a pressure support therapy.

FIGS. 1A and 1B, respectively, show front and rear views of an example electronic device 10 in the form of a smartphone which may be employed with, or as an element of, example embodiments in accordance with the present invention. Electronic device 10 includes a housing 12 having various electronic components, including a suitable processing device 14 (shown schematically in hidden line in FIG. 1B) disposed therein. Electronic device 10 further includes an/input output device positioned on a front face 16 of housing 12 in the form of a touchscreen 18 for providing data to, or receiving output from, processing device 14. Further input devices, e.g., side buttons 18A and 18B, may also be provided in electrical communication with processing device 14 for providing indications to processing device for carrying out predetermined functions thereof. Electronic device 10 further includes a first image capturing device in the form of a front facing camera 20 positioned on front face 16 facing away from housing 12 in a first direction D1, and a second image capturing device in the form of a rear-facing camera 22 positioned on a rear face 24 of housing 12, opposite front face 16, facing away from housing 12 in a second direction D2 opposite first direction D1. Front and rear facing cameras 20 and 22 are electrically connected to processing device 14 such that cameras 20 and 22 are both controlled by, and communicate captured image data to, processing device 14. As will be described further below, processing device 14 is structured to selectively actuate either one of cameras 20 and 22.

Processing device 14 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of electronic device 10. The memory portion can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Figure 2:
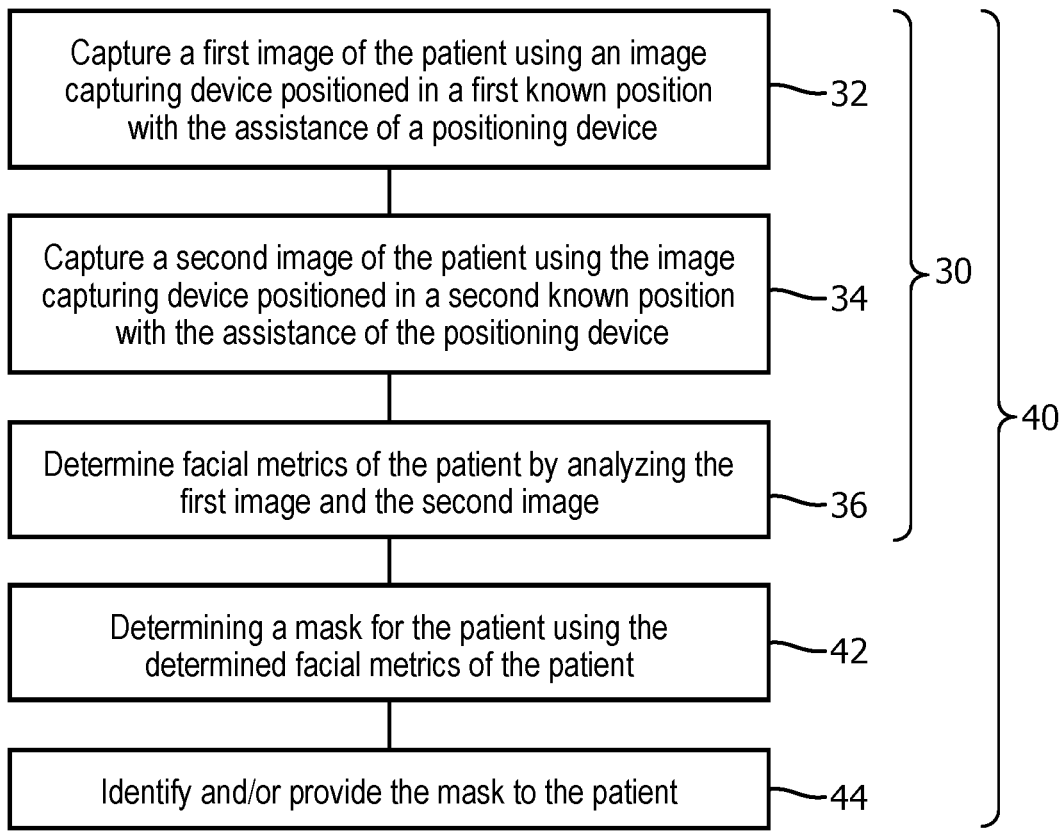
FIG. 2 is a flowchart showing a method for identifying a mask for a patient in accordance with one example embodiment of the present invention.

FIG. 2 is a flow chart showing basic steps of a method 30 in accordance with an example embodiment of the present invention, for identifying 3-D facial metrics of a patient. Such method may generally be carried out, for example, without limitation, by an image capturing device, e.g., without limitation, such as front or rear facing cameras 20 or 22 of electronic device 10, used in conjunction with a locating apparatus, such as described in various example below, which positions the patient's face a known distance from the image capturing device.

Method 30 begins at 32 wherein a first image of the person's face is captured by an image capturing device, such as image capturing devices 20 or 22 of electronic device 10 of FIG. 1, positioned at a first position relative to the person and at a predetermined first distance from the person. In an example embodiment of the present invention, such first image is a 2-D image.

Next, as shown at 34, a second image of the person's face is captured by the image capturing device positioned at a second position, different from the first position, relative to the person and at a predetermined second distance from the person. In an example embodiment of the present invention, such second image is a 2-D image. In one example embodiment of the present invention, the second predetermined distance is equal to the first predetermined distance, however, such distance may differ as long as the length of both the first and second predetermined distances are known. Embodiments of various devices which may be employed to ensure an image capturing device is positioned at such predetermined distances and/or locations while capturing the first and second images are described in detail below.

After the first and second images of the person's face are captured at 32 and 34, facial metrics of the user are determined, such as shown at 36, by analyzing the first image and the second image. During such analysis, the first and second images may be stitched together and triangulated to construct a 3-D geometry from which a custom CPAP mask for the user may be made or otherwise identified to the user. Alternatively, the 2D images could be used to create a 3-D spatial model using any number of other techniques known to one skilled in the art, e.g., for example, without limitation, through the use of disparity maps in the epipolar plane, volumetric deep neural networks (DNN), or generative adversarial network correlations. The determined facial metrics of the patient may be communicated to the patient or to another person or persons for use. Alternatively, the determined facial metrics of the patient may be employed in a larger method 40 of identifying a custom or semi-custom mask for a user, such as also shown in FIG. 2. Method 40 includes the method 30 as well as further determining a mask for the patient using the determined facial metrics, such as shown at 42. Then, as shown as 44, the mask is then identified and/or provided to the patient.

As an example, the patient may be provided with information, via any suitable form (e.g., electronically or via hardcopy), particularly specifying the mask (i.e., specifications which particularly identify the mask either from amongst other masks or how to construct from scratch or from components). For example, without limitation, a prescription for obtaining a particular mask or a CAD file or similar item containing instructions and/or dimensional information for constructing a custom mask may be provided. Alternatively, the mask may be identified to the patient by providing the patient with the actual mask, be it custom-made or an off-the-shelf item. In the case of a custom-made mask, a 3-D printer or other suitable automated manufacturing device may be used to provide the mask to the patient.

Having thus described example methods in accordance with the present concept for both determining facial metrics of person and further using such metrics to identify a custom or semi-custom mask for such person, examples of positioning devices in accordance with example embodiments of the present invention which may be employed in such methods will now be described.

A first example positioning device 50 is shown in the example embodiment of FIGS. 1 and 2 and may be an add on element or generally integrated into electronic device 10. Positioning device 50 includes an infrared (IR) projector 52 plus an IR sensor 54 in order to locate the distance between the image capturing device 20 and the patient (not shown). Alternatively, digital stereograph scanners, or a IR/visible light/stereograph mix may be employed to locate the focal length easily with passive user feedback. In one example embodiment of the present invention, positioning device 50 is used to guide the patient to position electronic device 10 a predetermined distance from the patient. In such embodiment an audial feedback is provided using an audial output 56 of electronic device to tell the subject to move the device into the right position. Such audial feedback may comprise a changing tune or beeping sound having a characteristic (e.g., volume, pace, pitch, etc.) which changes as electronic device 10 is moved toward or away from the desired predetermined distance. As an example, device 10 may emit a tune in various volumes, when device 10 moves closer to the correct position the volume reduces and once it hits the right position a loud beep will sound to notify the patient the desired position has been obtained. In another exemplary embodiment, the tune is replaced by a verbal command like "closer", or "further", and "stop".

As an alternative to an audial feedback, a visual feedback may be provided to the patient via an output on the device. In the case of electronic device 10, such visual feedback may be provided via touchscreen 18, an LED indicator 58, or any other element suitable for providing a visual output. As an example, a graphical or numerical distance indicator showing one or both of the current distance or distance to the predetermined distance may be displayed on touchscreen. In another example, LED indicator 58 may be flashed at varying speeds or may change colors depending on distance from the predetermined distance.

As an alternative to such passive feedbacks, an active element 59, shown in FIG. 1A as a string element of predetermined length, may be coupled at a first end 59A to electronic device 10. An opposite second end 59B is then held to the patient (e.g., to the chin or forehead) to position electronic device 10 the predetermined distance from the patient.

Figure 3:
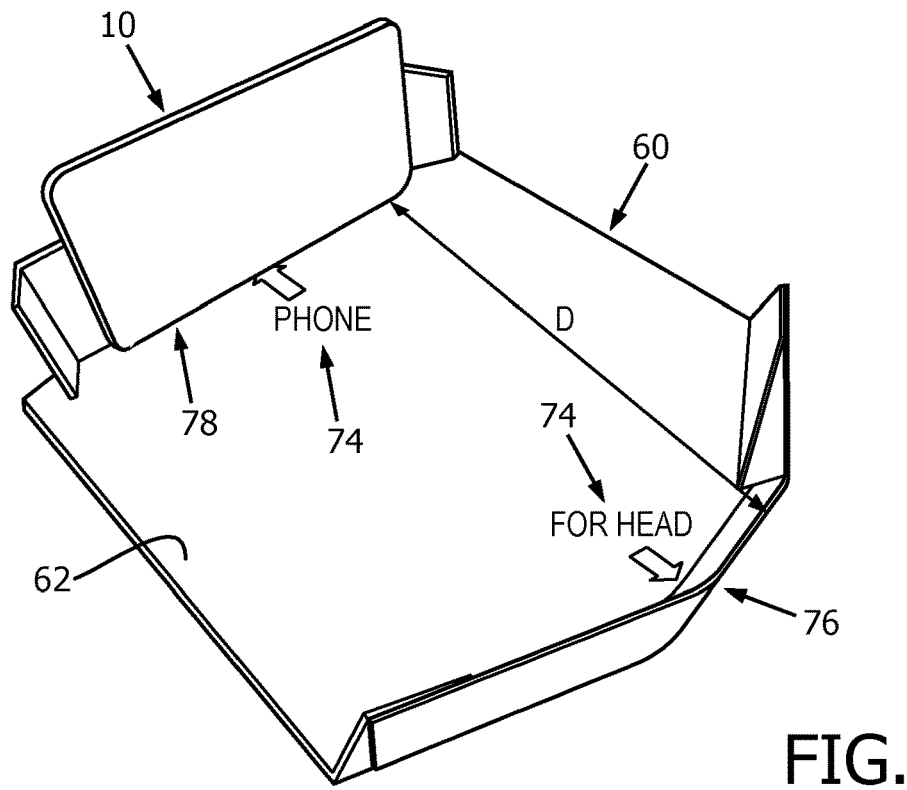
FIG. 3 is an example of a positioning device in accordance with one example embodiment of the present invention.
Figure 4:
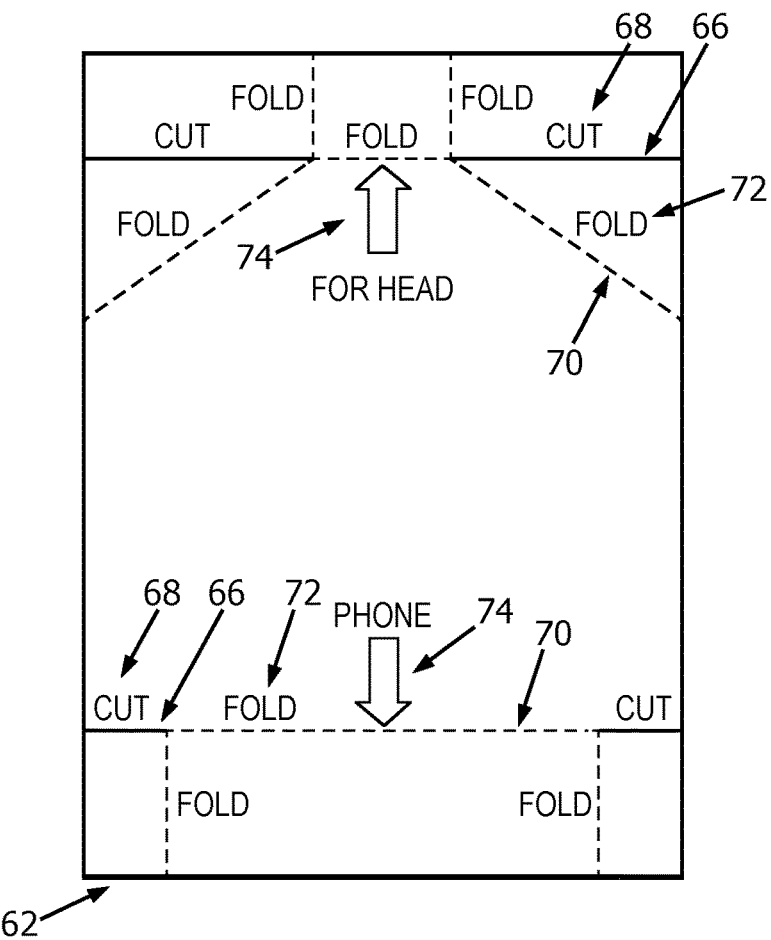
FIG. 4 is an example of a planar form in accordance with one example embodiment of the present invention from which the positioning device of FIG. 4 may be formed.

Another example positioning device 60 is shown in FIG. 3-5. Positioning device 60 may be formed from cardboard, heavy paper, plastic or other suitable material which can readily be sent to an end user (i.e., a patient) in an initial planar form 62, such as shown in FIG. 4. Planar form 62 may include primary indicia 64 for assisting the end user in forming positioning device 60. Primary indicia 64 may include a first graphical indication 66 of where cuts are to be made in form 62. In the example illustrated in FIG. 3 such first graphical indication 66 is in the form of solid lines. Optionally, such first graphical indication 66 may be accompanied by first instructive text 68. In the example illustrated in FIGS. 3 and 4 such first instructive text 68 is "CUT". Alternately, portions of form 62 may be pre-cut prior to being supplied to the patient, thus obviating the need to indicate where such cuts need to be made.

Primary indicia 64 may include a second graphical indication 70 of where folds are to be made in form 62. In the example illustrated in FIGS. 3 and 4 such second graphical indication 70 is in the form of dashed lines. Optionally, such second graphical indication 70 may be accompanied by second instructive text 72. In the example illustrated in FIGS. 3 and 4 such second instructive text 72 is "FOLD".

Planar form 62 may also include secondary indicia 74 for assisting the end user in using positioning device 60 in capturing digital images. In the example illustrated in FIGS. 3 and 4, such secondary indicia 74 include text with an accompanying arrow indicating where the users "FOREHEAD" and electronic "DEVICE" are to be positioned.

As an alternative to providing primary and secondary indicia 64 and 74 directly on form 62, such indicia 64 and 74 may instead be supplied in an electronic form (e.g., a downloadable or email-able electronic document) which can be printed by an end-user onto a suitable material (e.g., cardstock or other suitable material). Additional readily available materials (not labeled) such as, for example, without limitation, tape, staples, glue, etc. may be employed in forming positioning device 60 from form 62.

Figures 5A, 5B, 5C:
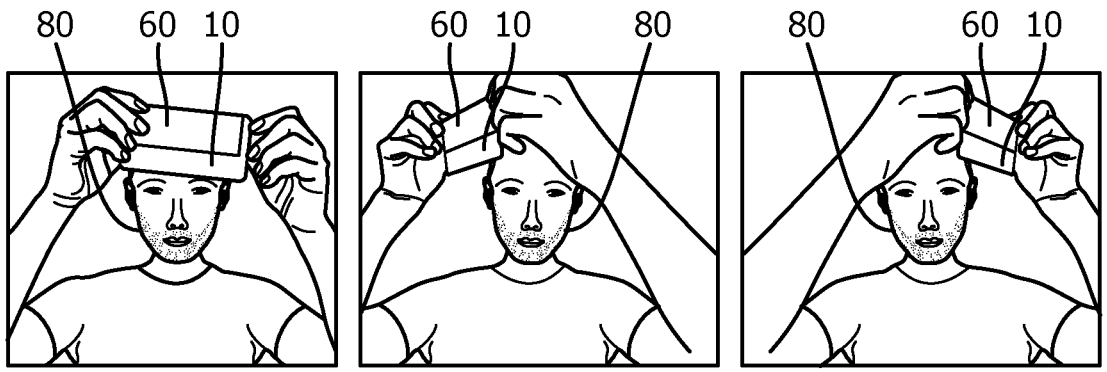
FIGS. 5A-5C show examples of the positioning device of FIG. 3 along with an image capturing device such as the electronic device of FIGS. 1A and 1B disposed in three different image capturing positions on a patient in accordance with an example embodiment of the present invention.

Referring to FIG. 3, once formed, positioning device 60 provides a first location 76 for placing against the patient when capturing images of the patient and a second location 78 for placing the image capturing device when capturing such images. Such locations 76 and 78 are spaced a predetermined distance D. In the example shown in FIG. 3, first location 76 is to be placed against the forehead of a patient and second location is for placement of a smartphone device, however, it is to be appreciated that other locations on a patient (e.g., without limitation, chin, neck, etc.) and/or placement of other image capturing devices (e.g., without limitation, electronic tablet, digital camera, etc.) may be provided depending on the desired application without varying from the scope of the present invention. FIGS. 5A-5C show examples of positioning device 60 along with an image capturing device such as electronic device 10 disposed in three different image capturing positions (e.g., center, right, and left) on a patient 80 in accordance with an example embodiment of the present invention.

Figure 6:
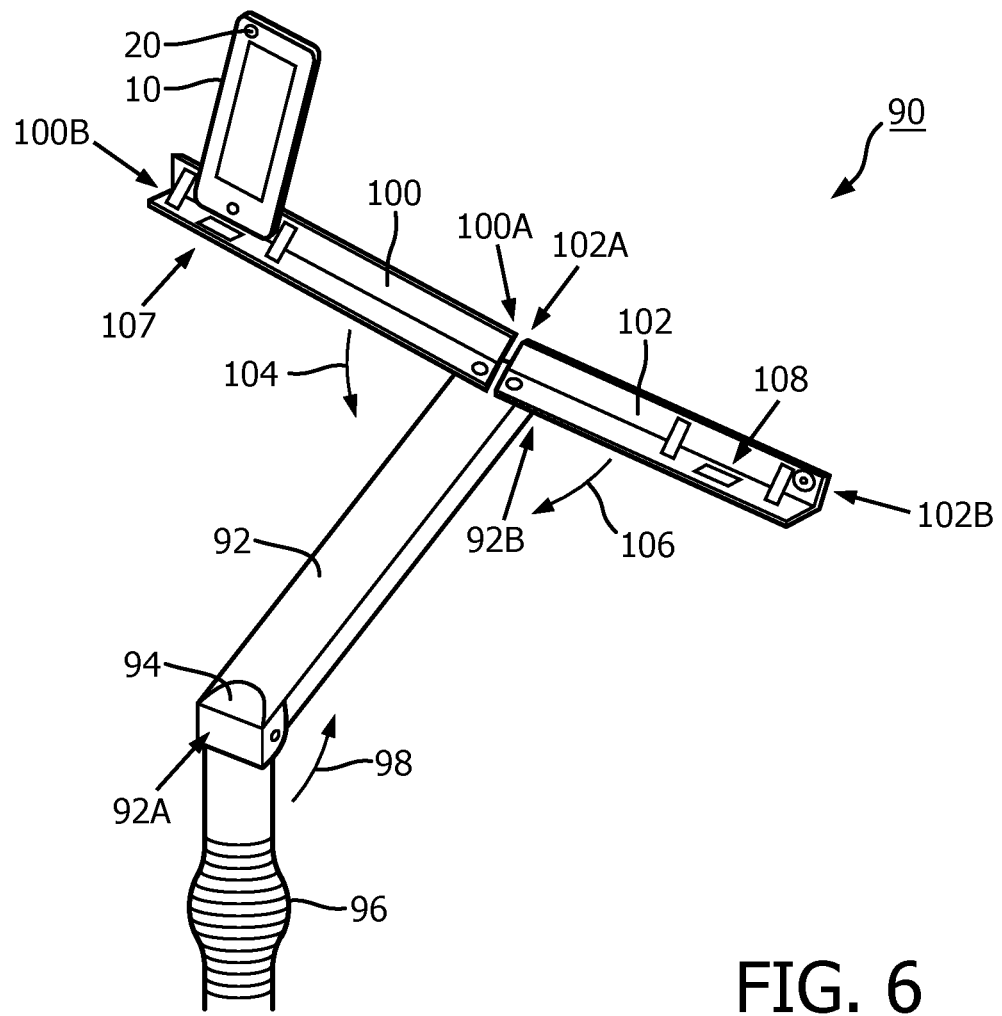
FIG. 6 is an example of another positioning device in accordance with one example embodiment of the present invention.
Figure 7:
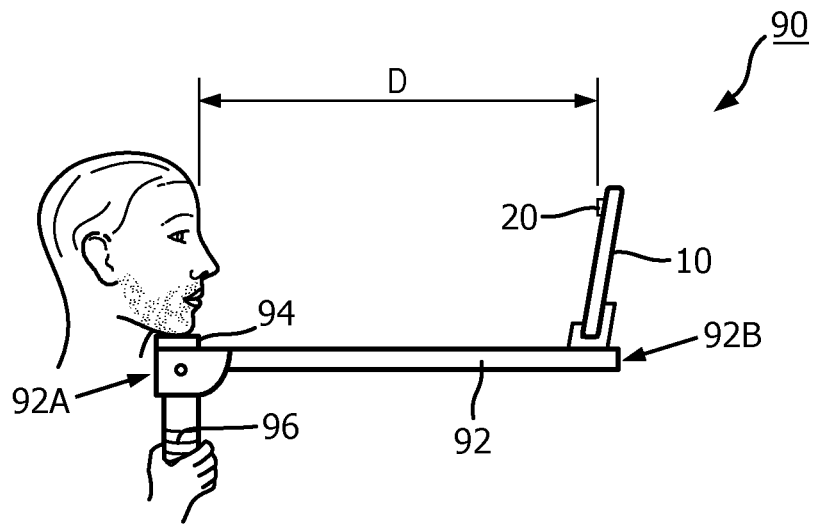
FIG. 7 is a side elevation view of the positioning device of FIG. 6 shown in use by a patient.

Yet another example of a positioning device 90 which may be employed in the aforementioned methods in capturing images of the patient is illustrated in FIGS. 6 and 7. Referring to FIG. 6, positioning device 90 includes a first elongate arm member 92 having a first end 92A and an opposite second end 92B. An area 94 for the patient to place their chin is disposed at or about first end 92A. Area 94 may include a cushion or other suitable device for receiving/ engaging the chin of the patient. A handle 96 structured to be grasped by the patient to hold positioning device 90 under the chin of the patient is coupled to, and extends from first arm 92 at or about first end 92A. Optionally, handle 96 may be rotatably coupled to first arm 92 such that handle 96 may be folded toward first arm 92, such as generally shown by arrow 98.

Continuing to refer to FIG. 6, positioning device 90 further includes a second elongate arm member 100 and a third elongate arm member 102. Second elongate arm member 100 includes a first end 100A coupled at or about second end 92B of first elongate arm member and an opposite second end 100B. Optionally, first end 100A may be rotatably coupled to first elongate arm member 92 such that second elongate arm member 100 may be folded toward first arm 92, such as generally shown by arrow 104. Similarly, third elongate arm member 102 includes a first end 102A coupled at or about second end 92B of first elongate arm member and an opposite second end 102B. Optionally, first end 102A may be rotatably coupled to first elongate arm member 92 such that third elongate arm member 102 may also be folded toward first arm 92, such as generally shown by arrow 106.

One or both of second and third elongate arm members 100 and 102 may include a number of regions (two regions 107 and 108 are shown in FIG. 6) for a patient to place an image capturing device (e.g., without limitation, electronic device 10) for capturing an image of the patient from a known position. Regions 107 and 108 may be delineated by indicia, physical structures, or other suitable means (not numbered). Optionally, one of second and third elongate arm members may include a remotely operable image capturing device 109, e.g., without limitation, a Bluetooth camera paired with electronic device 10, which may be used to capture one of the first image or the second image (with the other image being captured by the electronic device, e.g., electronic device 10).

As shown in FIG. 7, when in use, positioning device 90 serves to position an image capturing device, e.g., front-facing camera 20 of electronic device 10, a predetermined distance D from the patient having their chin disposed on area 94.

Figure 8:
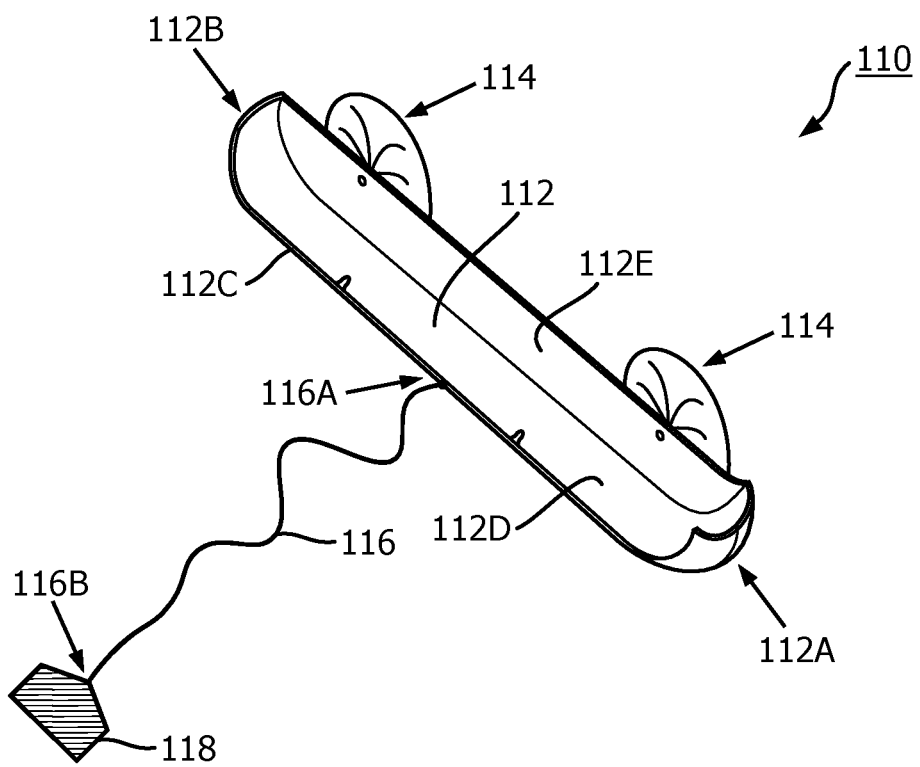
FIG. 8 is an example of yet another positioning device in accordance with one example embodiment of the present invention.
Figure 9:
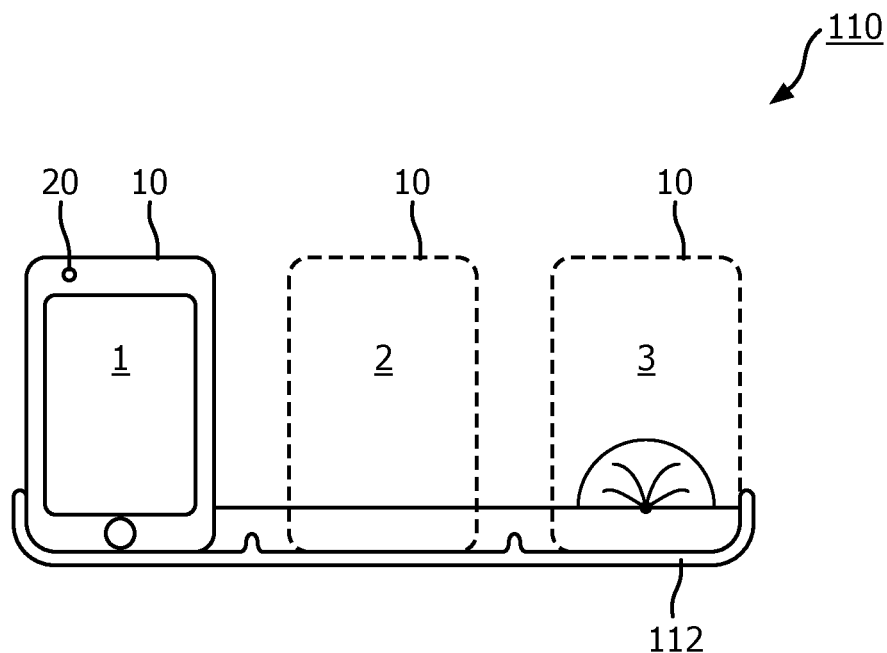
FIG. 9 is a front elevation view of the positioning device of FIG. 8 shown with an example image capturing device disposed thereon as well as two alternate positionings of the example image capturing device in accordance with one example embodiment of the present invention.
Figure 10:
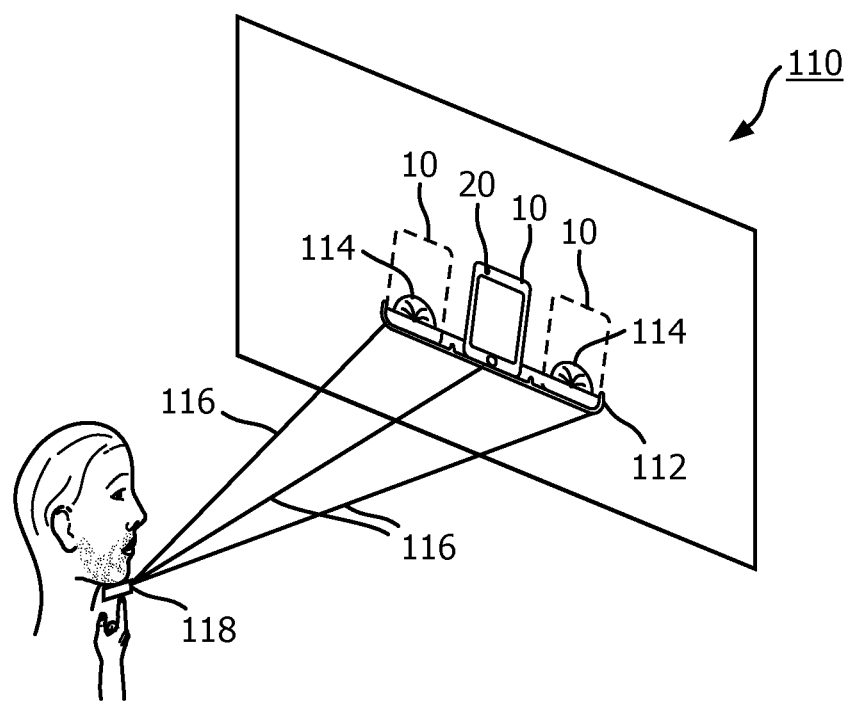
FIG. 10 is an isometric view of the positioning device of FIGS. 8 and 9 shown in use by a patient.

FIGS. 8-10 illustrate an example of yet another positioning device 110 which may be employed in the aforementioned methods in capturing images of the patient. Positioning device 110 includes an elongated tray member 112 having a first end 112A and an opposite second end 112B. Tray member 112 is generally J-shaped in cross-section having a front wall 112C which slightly rises up from a base portion 112D and a rear wall 112E which rises up a greater distance from base portion 112D than front portion 112C. Positioning device 110 further includes a plurality (two are shown in the illustrated example embodiment) of securement means 114 for securing tray member 112 to a vertical surface. In the example illustrated embodiment, each securement means 114 is in the form of a suction cup which may be employed in securing tray member 112 to a mirror or other suitably smooth surface. It is to be appreciated, however, that other securement means may be employed without varying from the scope of the present invention.

As shown in FIG. 9, tray member 112 is structured to generally support the base of an image capturing device, such as, without limitation, electronic device 10 of FIGS. 1A and 1B in a manner such that an image capturing device, such as front-facing camera 20 of electronic device 10 of FIGS. 1A and 1B, may be positioned in one of a plurality of predetermined positions (three are shown, labeled "1", "2", and "3") from which images may be captured of the patient.

In order to ensure the patient is positioned a predetermined distance from tray member 112, positioning device 110 further includes a number (one is shown in FIG. 8) of string members 116 coupled at a first end 116A to tray member 112. String member 116 further includes a patient engaging element 118 disposed an second end 116B opposite first end 116A for holding against the chin or other suitable portion of the patient. As shown in the example of FIG. 10, a plurality of strings 116 may be employed so as to center the patient (e.g., via triangulation) with tray member 112.

From the foregoing, it is to be appreciated that each of the example positioning devices described herein may be arranged to position an image capturing device and a person who is to be the subject of captured images in predetermined positions. From the images captured in such predetermined positions 3-D facial metrics of the person can readily be determined and a custom or semi-custom mask can then be identified or created for the person.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. It is also to be appreciated that the overall and/or cross sectional shapes of structures described herein are provided for exemplary purposes only and that such shapes may be varied without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method of determining facial metrics of a patient, the method comprising:
   capturing a first image of the patient with an image capturing device positioned in a first known position with the assistance of a positioning device;
   capturing a second image of the patient with the image capturing device positioned in a second known position different that the first known position with the assistance of the positioning device; and
   determining facial metrics of the patient by analyzing the first image and the second image, wherein the positioning device comprises:
   a first elongate arm member having a first end and an opposite second end;
   an area for the patient to place their chin disposed at or about the first end;

a handle coupled at or about the first end of the first elongate arm member, the handle structured to be grasped by the patient to hold the positioning device under the chin of the patient;

a second elongate arm member having a first end coupled at or about the second end of the first elongate arm member and an opposite second end, a third elongate arm member having a first end coupled at or about second end of the first elongate arm member and an opposite end, and a number of regions delineated on one or both of the second and third elongate arm members for receiving the image capturing device.

2. The method of claim 1, wherein the first image and the second image comprise 2D images.

3. The method of claim 1, wherein the image capturing device comprises a camera of an electronic device.

4. The method of claim 3, wherein the electronic device comprises one of a smartphone device or an electronic tablet.

5. The method of claim 4, wherein the smartphone or tablet comprises a front-facing camera and a rear-facing camera and wherein the first image and the second image are each captured using the front facing camera.

6. The method of claim 4, wherein the smartphone or tablet comprises a front-facing camera and a rear-facing camera and wherein the first image and the second image are each captured using the rear-facing camera.

7. The method of claim 1, wherein the positioning device further comprises:

an infrared projector; and an infrared sensor.

8. The method of claim 7, wherein the positioning device is structured to provide an audible or visual feedback to the patient.

9. The method of claim 1, wherein the positioning device includes secondary indicia indicating a position for engaging the patient with the positioning device and a position for placing the image capturing device in regard to the positioning device.

10. The method of claim 1, wherein one of the second or third elongate arm members includes a remotely operable image capturing device, and wherein capturing one of the first image or the second image is captured by the remotely operable image capturing device.

11. A method for identifying a mask for a patient, the method comprising:

capturing a first image of the patient with an image capturing device positioned in a first known position with the assistance of a positioning device;

capturing a second image of the patient with the image capturing device positioned in a second known position different that the first known position with the assistance of the positioning device;

determining facial metrics of the patient by analyzing the first image and the second image;

determining a mask for the patient using the determined facial metrics of the patient; and identifying the mask to the patient, wherein the positioning device comprises:

a first elongate arm member having a first end and an opposite second end;

an area for the patient to place their chin disposed at or about the first end;

a handle coupled at or about the first end of the first elongate arm member, the handle structured to be grasped by the patient to hold the positioning device under the chin of the patient;

a second elongate arm member having a first end coupled at or about the second end of the first elongate arm member and an opposite second end;

a third elongate arm member having a first end coupled at or about second end of the first elongate arm member and an opposite second end; and a number of regions delineated on one or both of the second and third elongate arm members for receiving the image capturing device.

12. The method of claim 11, wherein identifying the mask to the patient comprises providing the patient with a specification of the mask.

13. The method of claim 11, wherein identifying the mask to the patient comprises providing the patient with the mask.

* * * * *